(12) United States Patent
Boustany (10) Patent No.: US 6,821,995 B1
(45) Date of Patent: Nov. 23, 2004

(54) METHOD OF TREATING BATTEN DISEASE

(75) Inventor: Rose-Mary N. Boustany, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 10/148,859

(22) PCT Filed: Oct. 30, 2000

(86) PCT No.: PCT/US00/29913

§ 371 (c)(1),
(2), (4) Date: Oct. 7, 2002

(87) PCT Pub. No.: WO01/39760

PCT Pub. Date: Jun. 7, 2001

Related U.S. Application Data (60) Provisional application No. 60/168,287, filed on Dec. 1, 1999.

(51) Int. Cl.[7] .............................................. A61K 31/44
(52) U.S. Cl. .................................................... 514/352
(58) Field of Search ........................................ 514/352

(56) References Cited

U.S. PATENT DOCUMENTS

| | | | |
|---|---|---|---|
| 4,481,205 A | 11/1984 | von Bebenburg et al. | |
| 4,673,666 A | 6/1987 | Hettche et al. | ............... 514/23 |
| 4,834,965 A | 5/1989 | Martani et al. | |
| 5,162,346 A | 11/1992 | Lobisch et al. | |
| 5,284,861 A | 2/1994 | Lobisch et al. | |
| 5,503,845 A | 4/1996 | Goede et al. | |
| 5,721,258 A | 2/1998 | Schwarz et al. | |
| 5,959,115 A | 9/1999 | Olbrich et al. | |
| 6,034,111 A | 3/2000 | Pergande et al. | |
| 6,124,326 A | 9/2000 | Pergande et al. | |
| 6,194,000 B1 | 2/2001 | Smith et al. | |
| 6,610,324 B2 | 8/2003 | Stoll | |

FOREIGN PATENT DOCUMENTS

| | | |
|---|---|---|
| WO | WO 95/05175 | 2/1995 |
| WO | WO 97/49398 | 12/1997 |

OTHER PUBLICATIONS

Perovic, Sanja, et al., *Flupirtine increases the levels of glutathione and Bcl–2 in hNT (human Ntera/D1) neurons: mode of action of the drug–mediated anti–apoptotic effect*, European Journal of Pharmacology, vol. 317, pp. 157–164 (1996).

Puranam, K., et al., *Upregulation of Bcl–2 and Elevation of Ceramide in Batten Disease*, Neuropediatrics, vol. 28, pp. 37–41 (1997).

Riethmüller–Winzen, H., *Flupirtine in the treatment of post–operative pain*, Postgraduate Medical Journal, vol. 63, pp. 61–66 (1987).

Schwarz, M., et al., *Antiparkinsonian effect of flupirtine in monoamine–depleted rats*, Journal of Neural Transmission, vol. 103, pp. 581–590 (1996).

Müller, Werner E.G., et al., *Protection of Flupirtine of β–Amyloid–Indiced Apoptosis in Neuronal Cells in Vitro: Prevention of Amyloid–Indiced Glutathione Depletion*, Journal of Neurochemistry, vol. 68, pp. 2371–2377 (1997).

Perovic, Sanja, et al., *Pharmacological intervention in age–associated brain disorders by Flupirtine: Alzheimer's and Prion diseases*, Mechanisms of Ageing and Development, vol. 101, pp. 1–19 (1998).

Lane, Steven C., et al., *Apoptosis as the Mechanism of Neurodegeneration in Batten's Disease*, vol. 67, pp. 677–683 (1996).

Puranam, Kasturi L., et al., *CLN3 Defines a Novel Antiapoptotic Pathway Operative in Neurodegeneration and Mediated by Ceramide*, Molecular Genetics and Metabolism, vol. 66, pp. 294–308 (1999).

*Primary Examiner*—Phyllis Spivack
(74) *Attorney, Agent, or Firm*—Myers Bigel Sibley & Sajovec (57) ABSTRACT

A method of treating Batten disease in a subject in need thereof comprises administering to said subject an active agent selected from the group consisting of flupirtine and the pharmaceutically acceptable salts thereof in an amount effective to treat Batten disease in that subject. The administering step is preferably an oral administering step, and the active agent is preferably flupirtine maleate.

11 Claims, 9 Drawing Sheets

METHOD OF TREATING BATTEN DISEASE

RELATED APPLICATIONS

The present application is an application under 35 USC Section 371 of International Application Serial No. PCT/US00/29913, filed 30 Oct. 2000, which in turn claims the benefit of Provisional Application Ser. No. 60/168,287, filed 1 Dec. 1999, the disclosures of which are incorporated by reference herein as if set forth fully.

FIELD OF THE INVENTION

The present invention concerns methods of treating subjects afflicted with Batten disease.

BACKGROUND OF THE INVENTION

Batten disease is a group of neurodegenerative disorders characterized by cognitive decline, spasticity and seizures due to neuronal cell loss, and blindness due to retinitis pigmentosa. The juvenile form of Batten disease is an autosomal recessive neurodegenerative disease of childhood (R.-M. Boustany, et al., *Am. J. Med. Genet. Suppl.* 5: 47–58 (1988)). It is clinically characterized by onset at age 5–6 years with progressive blindness, generalized and myoclonic seizures, cognitive and motor decline and death in the mid to late twenties (R.-M. Boustany and E. H. Kolodny, *Rev. Neurol.* (Paris) 145: 105–110 (1989); R.-M. Boustany, *Am. J. Med. Genet.* 42: 533–535 (1992); R.-M. Boustany and P. Filipek, *J. Inher. Metab. Dis.* 16: 252–255 (1993)). No suitable treatments for Batten disease are currently available. Therefore, there is an urgent need for the development of new ways to treat Batten disease.

SUMMARY OF THE INVENTION

A first aspect of the present invention is a method of treating Batten disease in a subject in need thereof. The method comprises administering to said subject an active agent selected from the group consisting of flupirtine and the pharmaceutically acceptable salts thereof in an amount effective to treat Batten disease in that subject. The administering step is preferably an oral administering step, and the active agent is preferably flupirtine maleate.

A second aspect of the present invention is the use of flupirtine or a pharmaceutically acceptable salt thereof for the preparation of a medicament for the treatment of Batten disease.

Flupirtine (available in some regions in the flupirtine maleate form as the drug Katodolon® from ASTAmedica) was developed as a centrally acting, non-opiate analgesic. It is currently in use in Germany, Brazil, Italy and other countries. It has been used in adults and children safety and chronically for over 12 months without undue side effect or addiction. It has been shown to counteract apoptosis in retinal pigment epithelial cells and neuronal cells in culture. It has been shown to reduce the area of ischemia induced by stroke in rats pretreated with it. It has been shown to have anticonvulsant effects and very powerful muscle relaxant effects as well. The use of flupirtine in the treatment of Batten disease has neither been suggested nor disclosed.

The present invention is explained in greater detail in the specification set forth below.

BRIEF DESCRIPTION OF THE DRAWINGS

FIG. 3 shows the effect of mitochondrial membrane transition in INCL lymphoblast (FIG. 3A), LINCL fibroblast (FIG. 3B), and JNCL lymphoblast (FIG. 3C) cells untreated (Panel 1), treated with etoposide only (Panel 2) and treated with flupirtine prior to treatment with etoposide (Panel 3). Outlines of cells are shown; areas of yellow-red aggregates are indicated by heavier lines and crosshatching. Cells were visualized by fluorescent microscopy.

DETAILED DESCRIPTION OF PREFERRED EMBODIMENTS

The term "Batten disease" as used herein includes all forms of Batten disease (neurogenetic disease with a degenerative component), including but not limited to late infantile, juvenile, Costa Rican variant infantile, etc.

The term "treat" as used herein refers to any type of treatment that imparts a benefit to a patient afflicted with a disease, including improvement in the condition of the patient (e.g., in one or more symptoms), delay in the progression of the disease, etc.

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes.

While the present invention is primarily concerned with the treatment of Batten disease and is described with respect to the treatment of Batten disease herein, it will be appreciated that the methods, compositions, dosages, routes of administration, steps, etc. described herein may also be used to treat other neurodegenerative diseases such as Alzheimer disease, Parkinson disease, amyotrophic lateral sclerosis, spinal muscular atrophy, and spinocerebellar degenerations types 1–9.

1. Active Compounds.

Flupirtine (2-amino-3-ethoxycarbonylamino-6-(p-fluorobenzylamino)-pyridine) and pharmaceutically acceptable salts thereof (e.g., hydrochloride, maleate, and gluconate salts) are known and can be prepared in accordance with known techniques. See, e.g., Merck Index No. 4227 ($12^{th}$ Ed. 1996).

2-amino-3-ethoxycarbonylamino-6-(p-fluorobenzylamino)-pyridine-hydrochloride is described in German Patent No. 1,795,858.

2-amino-3-ethoxycarbonylamino-6-(p-fluorobenzylamino)-pyridine maleate (flupirtine maleate), along with pharmaceutical formulations thereof, is described in U.S. Pat. No. 4,481,205 to VonBebenburg et al.

2-amino-3-ethoxycarbonylamino-6-(p-fluorobenzylamino)-pyridine gluconate, along with pharmaceutical formulations thereof, is described in U.S. Pat. No. 4,673,666 to Hettche et al.

2-amino-3-ethoxycarbonylamino&(p-fluorobenzylamino)-pyridine maleate, along with pharmaceutical formulations thereof, and particular routes of synthesis thereof leading to production of the A crystal modification, is described in U.S. Pat. No. 5,959,115 to Olbrich et al.

Flupirtine maleate is formed as a mixture of two crystalline forms A and B; mixtures containing 60 to 90 percent or more of the A form are preferred.

Applicant specifically intends that the disclosure of all United States patent references cited herein be incorporated by reference herein in their entirety.

2. Pharmaceutical Formulations.

The active compounds described above may be formulated for administration in a pharmaceutical carrier in accordance with known techniques. See, e.g., Remington, The Science And Practice of Pharmacy ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then; if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral or vaginal administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2 M active ingredient.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration. Oral administration of the active agent is currently preferred.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art.

In general, for human subjects, the active agent is administered in a dosage of 100, 200, 300, or 400 milligrams per day up to 2,000, 3,000, or 5,000 milligrams per day. The dosage may be given in a single administration or may be subdivided into multiple administrations (e.g., 3, 4, 5 or 6 administrations per day, to achieve a total dosage as described above). Such dosage ranges are particularly preferred for flupirtine maleate, given by oral administration.

In one particularly preferred embodiment, flupirtine maleate is given orally to human patients at a dose of from 600 to 1800 milligrams a day, administered as six separate dosages of 100 to 300 milligrams each.

In another particularly preferred embodiment, flupirtine maleate is given orally to human patients as a capsule containing from 50 to 150 milligrams of flupirtine maleate, preferably 100 milligrams of flupirtine maleate, up to a 400 to 1200 or 1800 milligrams a day (most preferably up to 600 milligrams a day).

In another particularly preferred embodiment, flupirtine maleate is given rectally to human children as a suppository containing from 50 to 100 mg flupirtine maleate, preferably 75 mg flupirtine maleate, up to a maximum dosage of 200 to 500 milligrams per day (most preferably up to 300 milligrams per day).

In another particularly preferred embodiment, flupirtine maleate is given rectally to human adults as a suppository containing from 100 to 200 mg flupirtine maleate, preferably 150 mg flupirtine maleate, up to a maximum dosage of 700 to 1200 milligrams per day (most preferably up to 900 milligrams per day).

The foregoing is illustrative of the present invention, and is not to be construed as limiting thereof. The invention is defined by the following claims, with equivalents of the claims to be included therein.

EXAMPLE 1

Establishment of a Batten Disease Cell Line

Figure 1A:
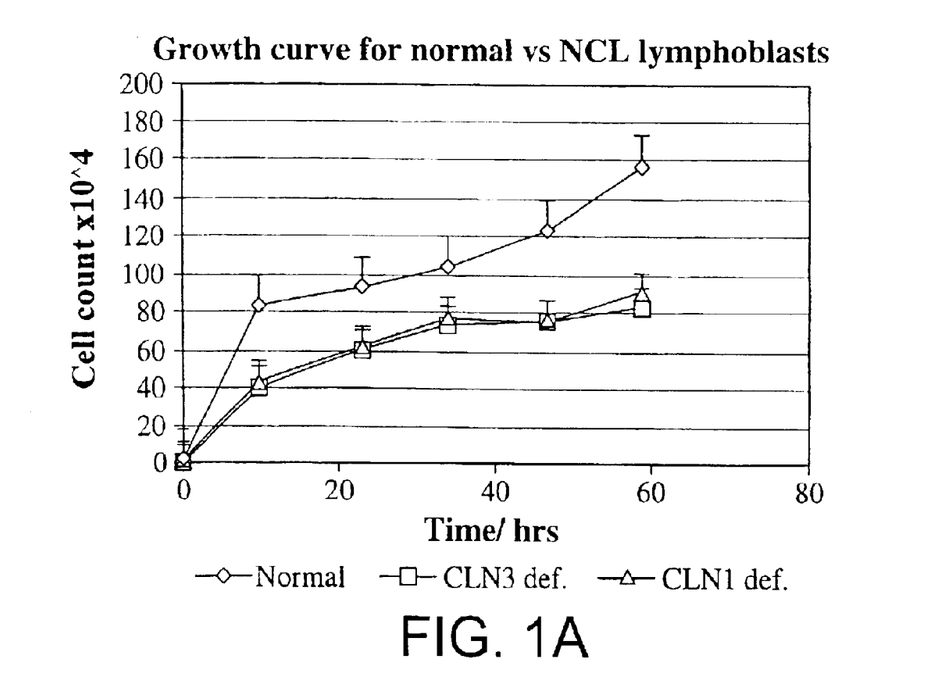
FIG. 1A shows the growth curves of CLN1 and CLN3 deficient lymphoblasts. Cell counts were assessed using trypan blue stain.
Figure 1B:
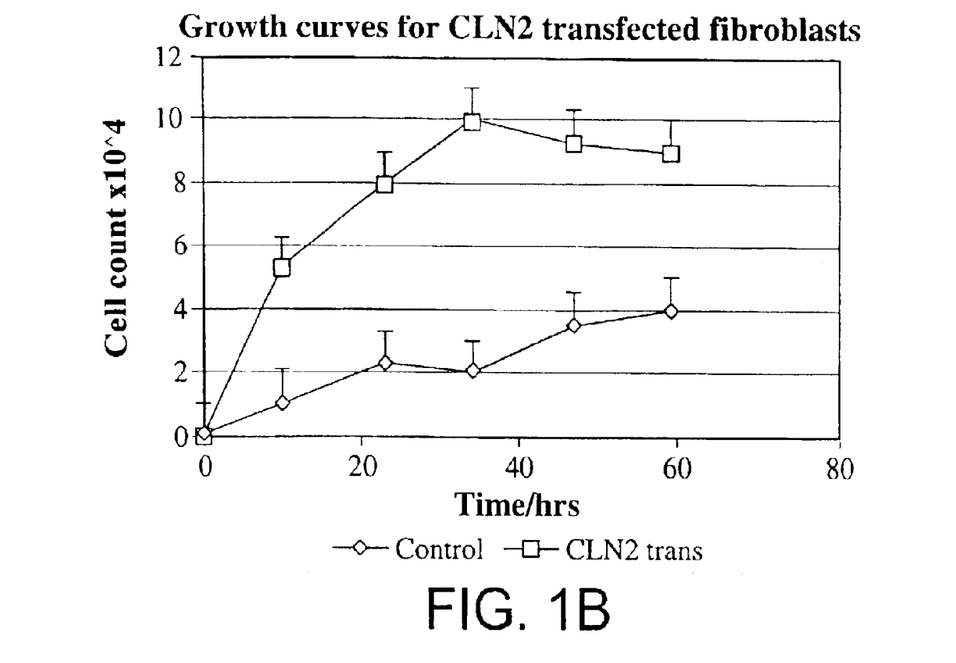
FIG. 1B shows growth curves of CLN2 deficient fibroblasts transfected with an empty plasmid compared to the same cell line transfected with the CLN2 gene.
Figure 1C:
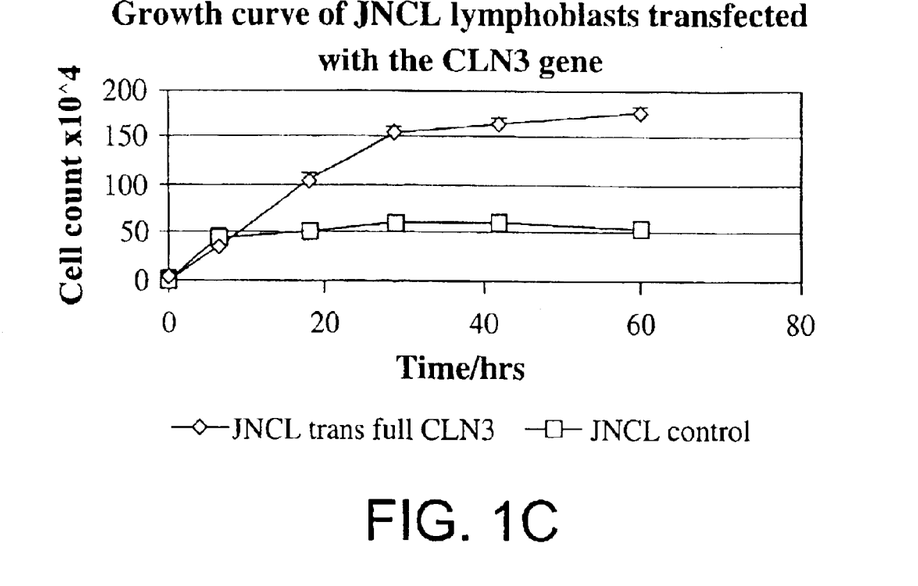
FIG. 1C shows growth curves for JNCL lymphoblasts transfected with the CLN3 gene. Control cells were transfected with an empty plasmid. Cell counts were assessed by trypan blue staining and counting.
Figure 2:
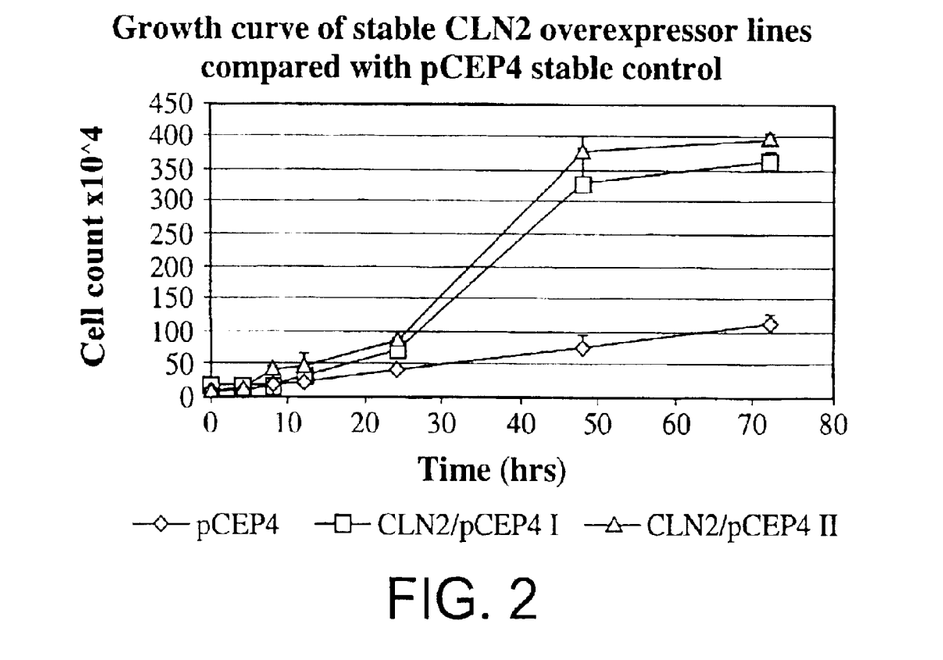
FIG. 2 shows growth curves of cell lines stably overdressing cln2 compared to cell lines transfected with the pCEP4 plasmid control. Cell counts were assessed by trypan blue staining and counting.

Cell lines were derived from three different forms of Batten disease. These lymphoblast cell lines were a CLN1 deficient or infantile form, a CLN2 deficient or late infantile form, and CLN3 deficient or juvenile form. Growth studies were conducted to demonstrate that these cell lines have impaired or slowed growth rates (FIG. 1A). When compared to normal lymphoblasts, the CLN1 and CLN3 cell lines had a reduced growth rate. This growth defect could be complemented when a plasmid harboring CLN2 or CLN3 were transfected into cell lines deficient in CLN2 (FIG. 1B) and CLN3 (FIG. 1C), respectively.

It was next determined whether overexpression of CLN2 could enhance the growth rate of a neuronal precursor cell line. Transfection and stable overexpression of CLN2, residing on plasmid pCEP4, was accomplished in a neuronal cell line and growth studies revealed that growth was enhanced. These results suggest that not only CLN3, but CLN2 and CLN1 positively modulate growth.

EXAMPLE 2

Protective Effects of Flupirtine from Etoposide-Induced Apoptosis

Batten disease-derived cell lines were tested for their susceptibility to apoptosis induced by etoposide and whether flupirtine had any protective effect against apoptosis. Cells derived from infantile Batten disease (INCL or CLN1 deficient), cells derived from late infantile Batten disease (LINCL or CLN2 deficient), and cells derived from juvenile Batten disease (JNCL or CLN3 deficient) received an 18 hour incubation in 30 $\mu$M etoposide with and without a pre-treatment with 20 $\mu$M flupirtine. As a control, cells were also left untreated. Cells were then stained with JC-1 fluorescent stain, which is a mitochondrial membrane potential-sensitive dye. When cells are alive, the mitochondrial potential is maintained and the mitochondria appear green. At the commitment point of apoptosis, proapoptotic agents like etopside cause a drop in mitochondrial membrane potential and the mitochondria appear yellow-red due to the formation of J-aggregates. Pretreatment of cells with 20 $\mu$M flupirtine or Katodolon® (ASTAmedica) prevents this drop in mitochondrial membrane potential hence preventing apoptosis and the cells remain green.

Figure 3A:
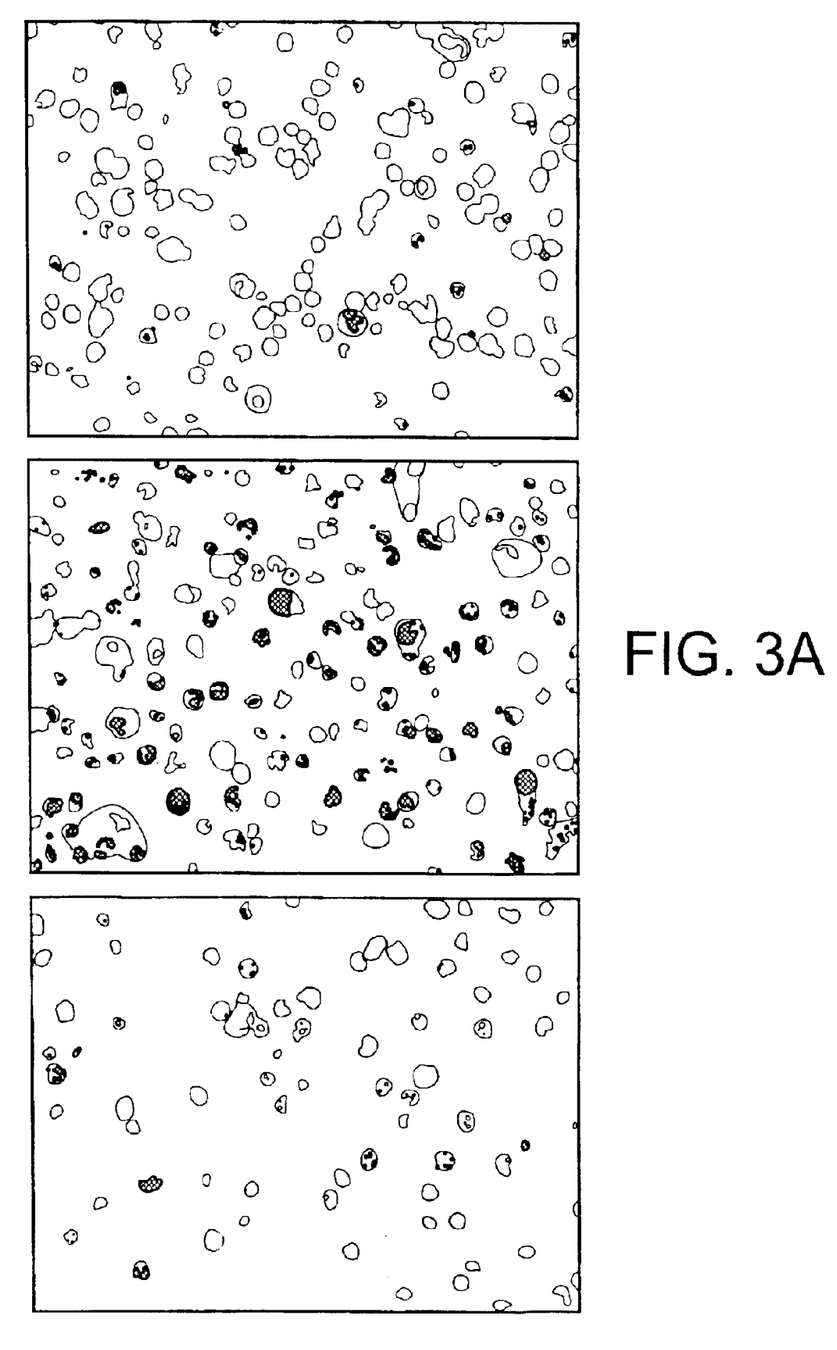
Figure 3B:
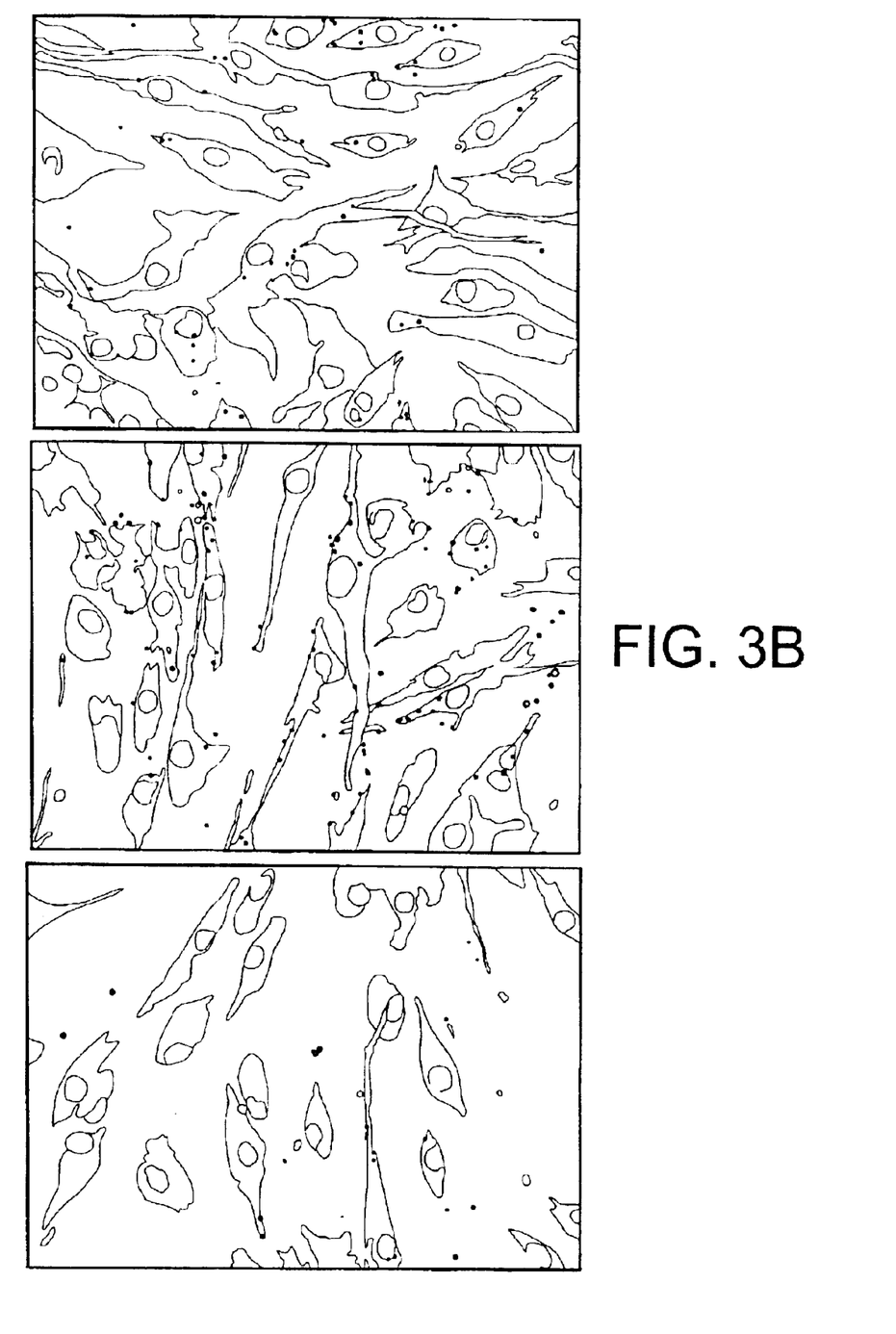
Figure 3C:
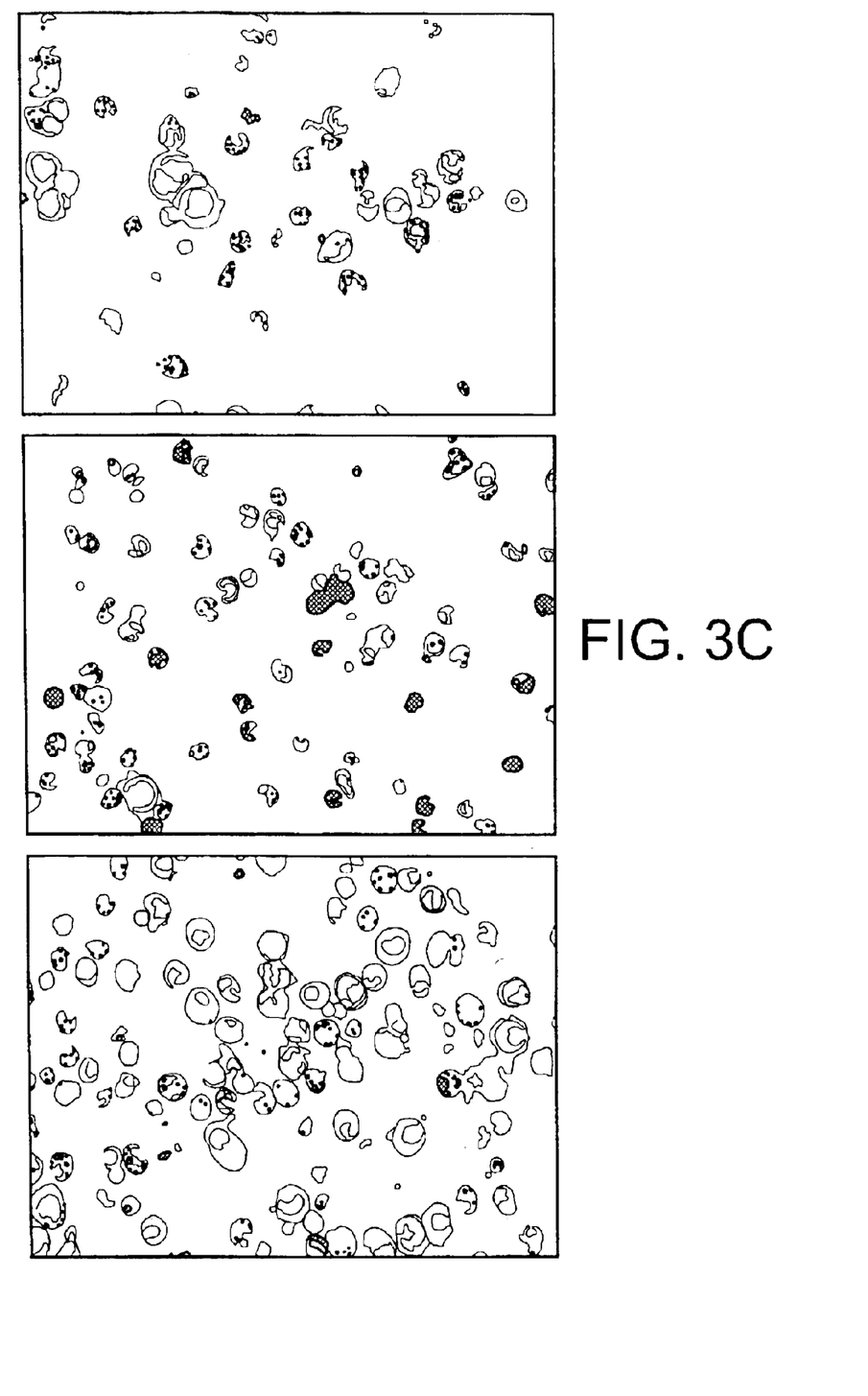

INCL cells treated with etoposide alone formed many yellow-red aggregates compared to no aggregates seen in the untreated and flupirtine pretreated cells (FIG. 3A). Likewise, LINCL and JNCL cells treated with etoposide alone formed many yellow-red aggregates compared to no aggregates seen in the untreated and flupirtine pretreated cells (FIG. 3B and 3C, respectively). The results of this experiment indicated that all three cell lines were particularly susceptible to apoptosis induced by etoposide and that flupirtine had a protective effect from etoposide-induced apoptosis.

Figure 4:
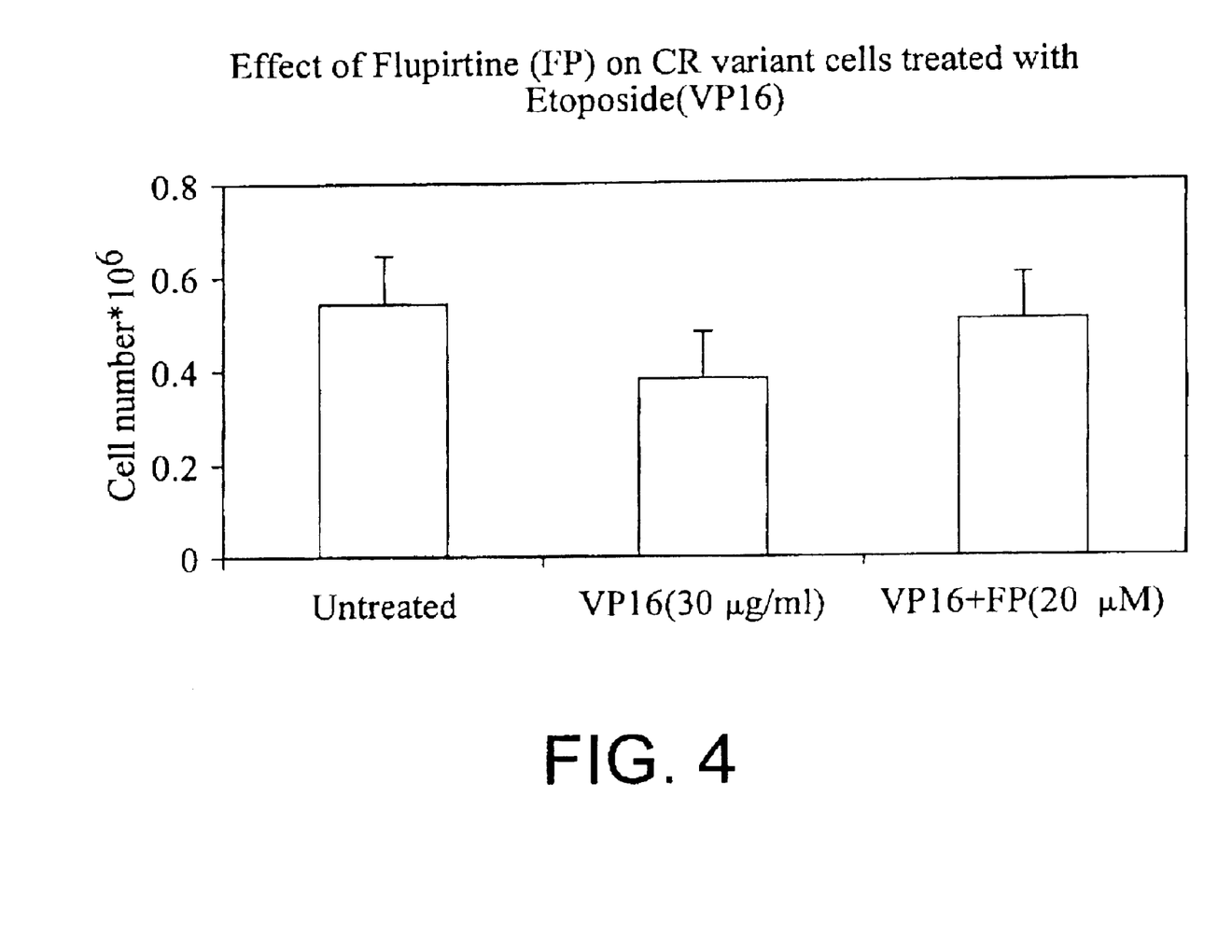
FIG. 4 shows flupirtine protection against etoposide-induced apoptosis in Costa Rican Batten disease-derived fibroblasts. Graph represents number of living cells after treatments indicated.

Cells derived from Costa Rican Batten disease (CLN6 deficient) were also tested for their response to etoposide. The CLN6 gene remains uncharacterized, though linked to chromosome 15. The results of this experiment indicated that this cell line was also protected from etoposide-induced apoptosis by pretreatment with flupirtine (FIG. 4).

Figure 5A:
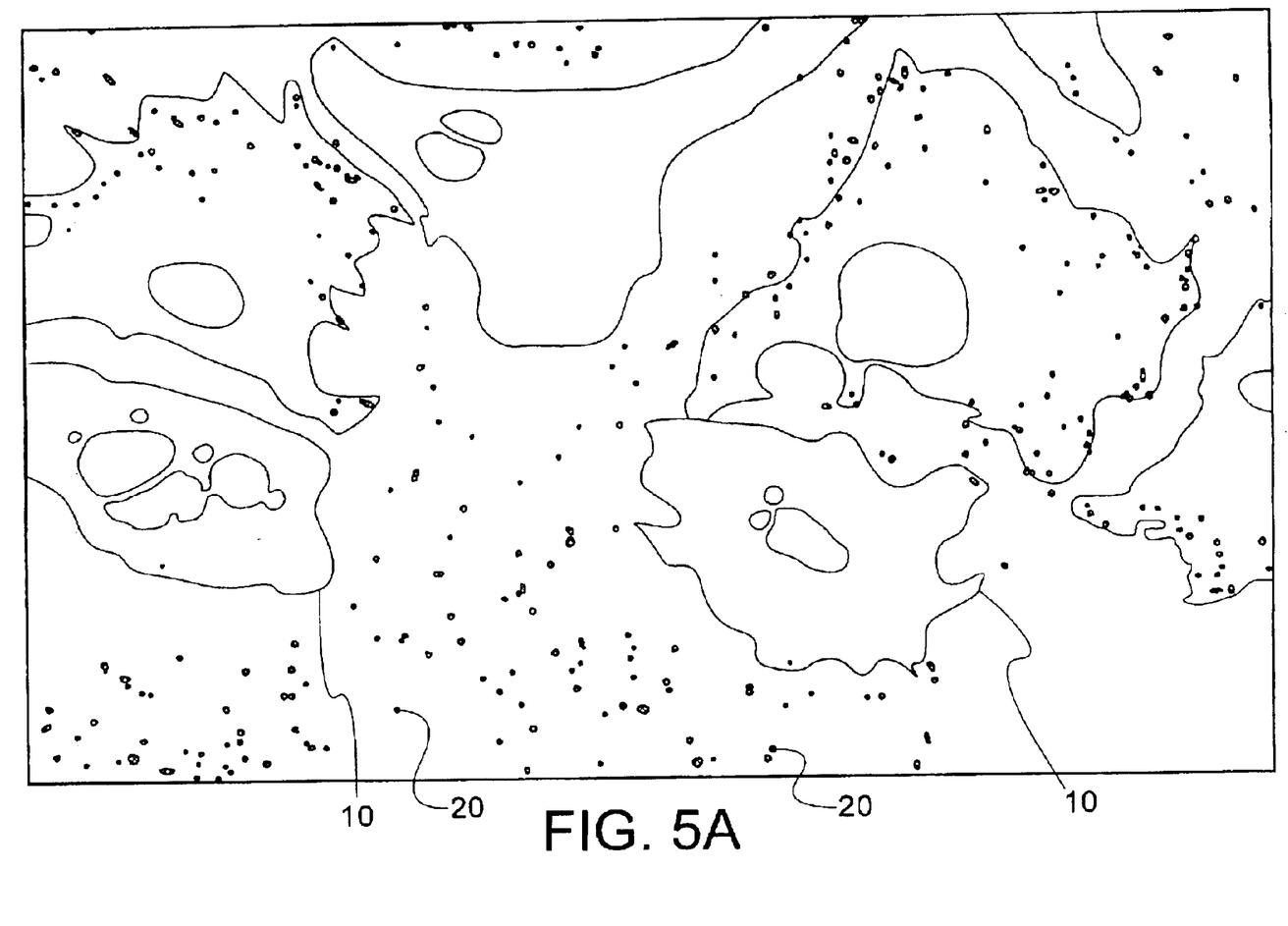
FIG. 5 shows the effect of mitochondrial membrane transition in differentiated neurons (hNT) cells untreated (Panel 1), treated with etoposide only (Panel 2) and treated with flupirtine prior to treatment with etoposide (Panel 3). Outlines of cells are shown (10); areas of yellow-red aggregates are indicated by heavier lines and crosshatching (20). Cells were visualized by fluorescent microscopy.
Figure 5B:
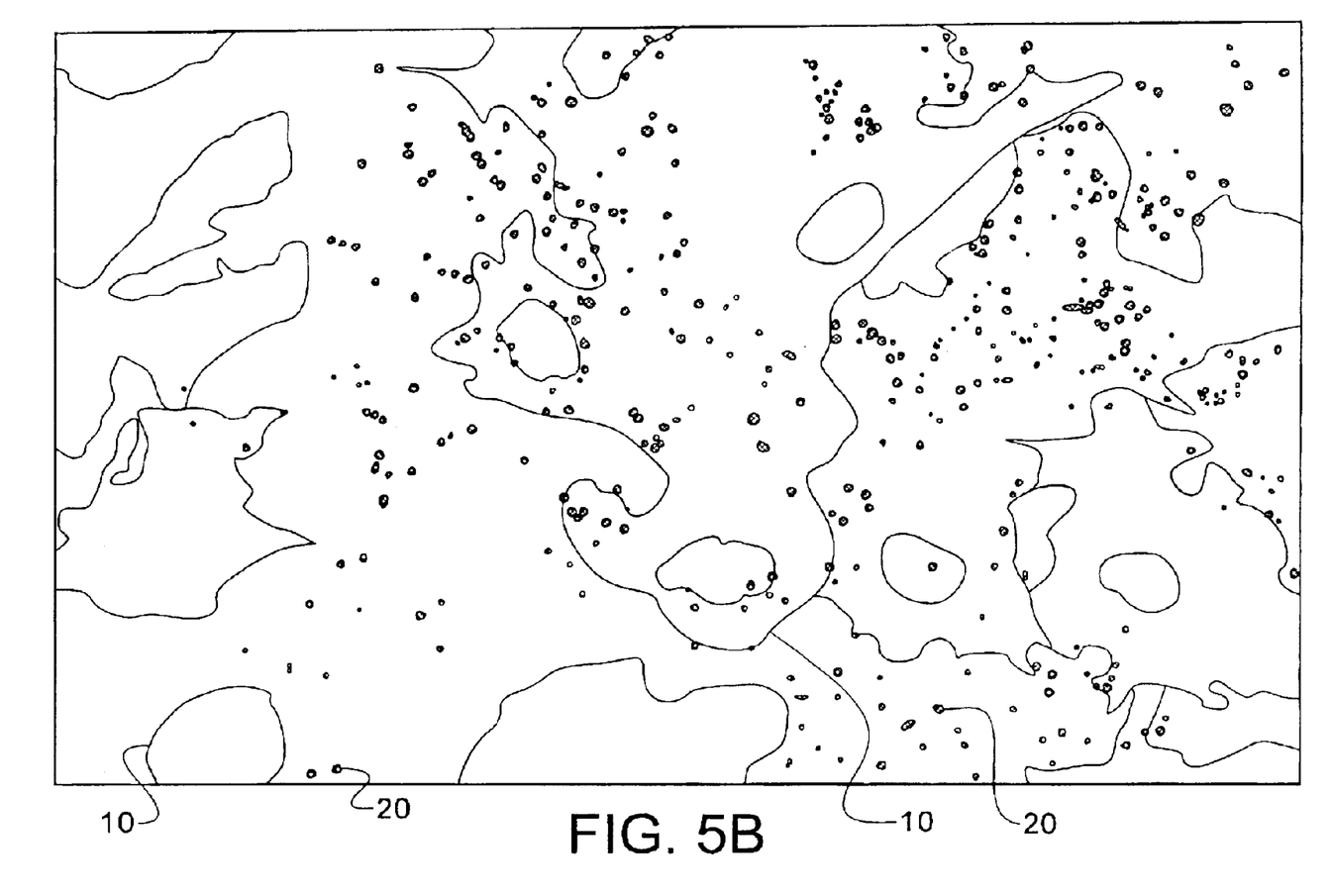
Figure 5C:
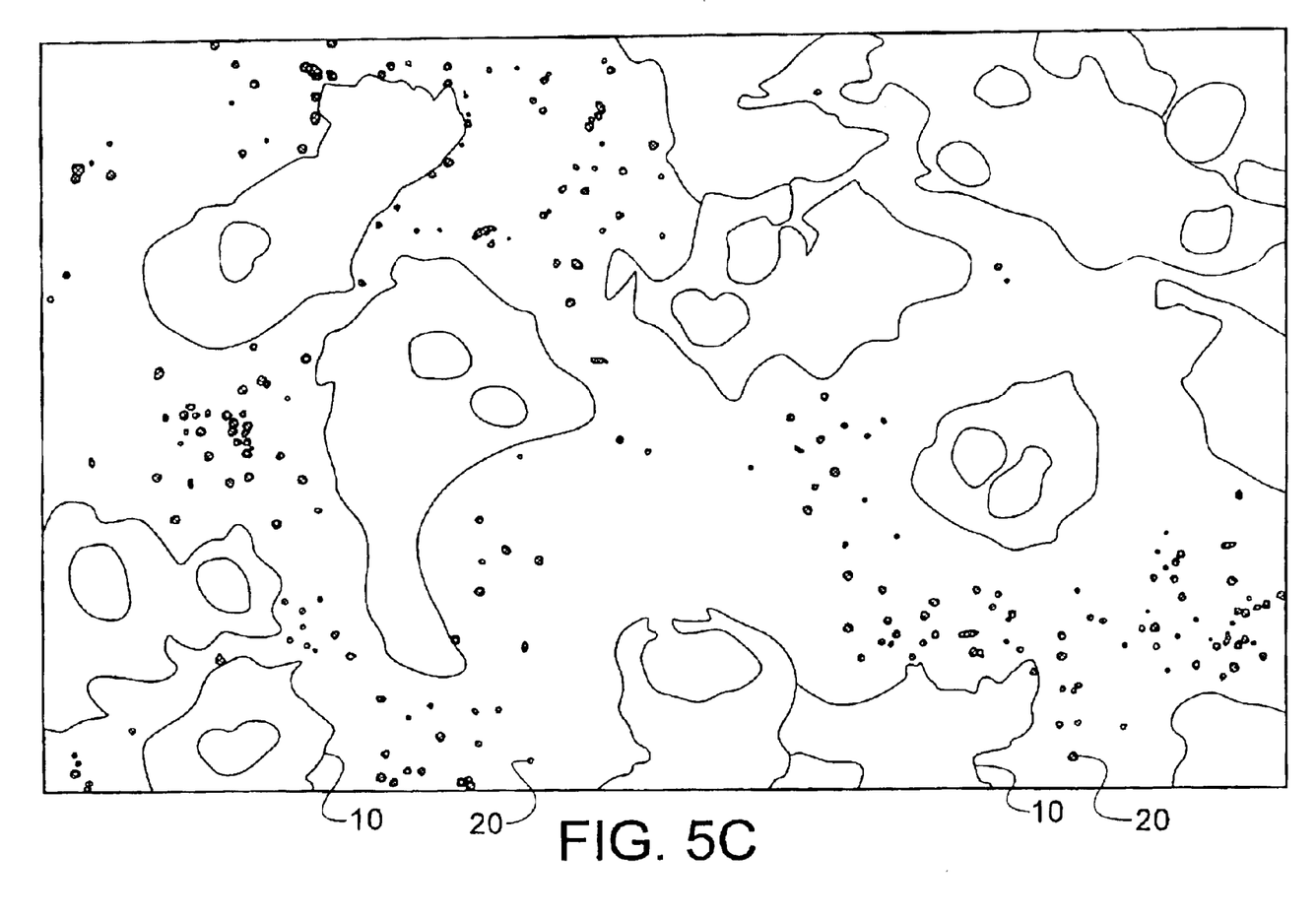

Finally, human post-mitotic neuronal cells were tested for thier response to flupirtine and etoposide-induced apoptosis. NT2 cells were treated with retinoic acid, then mitotic inhibitors for 6 weeks to become hNT neurons that were fully differentiated. Next, the hNT neurons received an 18 hour incubation in 20 $\mu$M etoposide with and without a pre-treatment with 10 $\mu$M flupirtine. These experiments indicated that flupirtine completely blocked etoposide-induced apoptosis in human post-mitotic, fully-differentiated neurons (FIG. 5).

Cell counts were conducted for to determine the percentage of cells showing J-aggregates (TABLE 1).

TABLE 1

| Cell Line | Untreated | Etoposide | Etoposide + Flupirtine |
|---|---|---|---|
| LINCL | 2.6% | 100% | 0% |
|  | 3.0% | 96% | 1.8% |
| INCL | 1.7% | 61% | 6.7% |
|  | 8.9% | 51% | 10.8% |
| JNCL | 20% | 64% | 21% |
|  | 20.4% | 58.4% | 9.5% |

Results are shown for two patient cell lines for each of the variants. Each cell line had a sample that was untreated, treated with Etoposide, and treated with Flupirtine in addition to Etoposide. The numbers of cells showing J-aggregates indicates the number of cells that are apoptosis-ready but are still viable. For the LINCL cell line, the protection afforded by Flupirtine was almost complete, whereas the INCL cell line received a 5 to 9-fold protection and the JNCL cell line received a 3 to 6-fold protection.

What is claimed is:

1. A method of treating Batten disease in a subject in need thereof, comprising administering said to subject an active agent selected from the group consisting of flupirtine and the pharmaceutically acceptable salts thereof in an amount effective to treat Batten disease.

2. A method according to claim 1, wherein said administering step is an oral administering step.

3. A method according to claim 1, wherein said active agent is flupirtine maleate.

4. A method according to claim 1, wherein said active agent is administered to said subject in an amount ranging from about 100 to about 5000 milligrams per day.

5. A method according to claim 1, wherein said subject is afflicted with late infantile Batten disease.

6. A method according to claim 1, wherein said subject is afflicted with juvenile Batten disease.

7. A method according to claim 1, wherein said subject is afflicted with Costa Rican variant infantile Batten disease.

8. A method of treating Batten disease in a subject in need thereof, comprising orally administering said subject flupirtine maleate in an amount ranging from about 100 to about 5000 milligrams per day.

9. A method according to claim 8, wherein said subject is afflicted with late infantile Batten disease.

10. A method according to claim 8, wherein said subject is afflicted with juvenile Batten disease.

11. A method according to claim 8, wherein said subject is afflicted with Costa Rican variant infantile Batten disease.

* * * * *